United States Patent [19]

Becher et al.

[11] Patent Number: 5,336,671

[45] Date of Patent: Aug. 9, 1994

[54] FUNGICIDAL COMPOSITIONS CONTAINING BENZYL-TRIS(ARYL)PHOSPHONIUM SALTS

[75] Inventors: Heinz-Manfred Becher, Bingen; Guido Albert, Hackenheim; Jürgen Curtze, Johannisberg, all of Fed. Rep. of Germany

[73] Assignee: Shell Research Limited, United Kingdom

[21] Appl. No.: 761,970

[22] PCT Filed: Feb. 20, 1991

[86] PCT No.: PCT/EP91/00293

§ 371 Date: Oct. 18, 1991

§ 102(e) Date: Oct. 18, 1991

[87] PCT Pub. No.: WO91/13073

PCT Pub. Date: Sep. 5, 1991

[30] Foreign Application Priority Data

Mar. 1, 1990 [EP] European Pat. Off. ......... 90103999

[51] Int. Cl.$^5$ .................. C07F 9/54; A01N 57/34
[52] U.S. Cl. .................. 514/96; 514/112; 514/114; 514/116; 514/120; 514/121; 514/125; 514/126; 514/129; 514/131
[58] Field of Search ............... 568/9, 11; 514/75, 130, 514/75, 80, 112, 124, 96, 114, 116, 120, 121, 125, 126, 129, 131; 562/45, 477; 423/366; 558/10; 548/211

[56] References Cited

U.S. PATENT DOCUMENTS

| | | | |
|---|---|---|---|
| 2,946,824 | 7/1960 | Chiddix | 568/9 |
| 3,268,323 | 8/1966 | Goyette et al. | 71/86 |
| 3,517,067 | 6/1970 | Stern | 568/9 |
| 3,625,999 | 12/1971 | Priestley | 260/505 R |
| 3,662,065 | 5/1972 | Bulske et al. | 514/75 |
| 3,998,754 | 12/1976 | Oswald | 252/356 |
| 4,187,300 | 2/1980 | Kinnamon | 514/75 |
| 4,188,380 | 2/1980 | Oswald | 424/198 |
| 4,251,522 | 2/1981 | Brown . | |
| 4,264,593 | 4/1981 | Sukman | 568/9 |
| 4,849,438 | 7/1989 | Fruchijima et al. | 548/211 |
| 4,943,380 | 7/1990 | Sugiura et al. | 568/9 |

| | | | |
|---|---|---|---|
| 5,102,874 | 4/1992 | Lintner et al. | 568/9 |

FOREIGN PATENT DOCUMENTS

| | | | |
|---|---|---|---|
| 0028493 | 5/1981 | European Pat. Off. . | |
| 0073574 | 9/1983 | European Pat. Off. . | |
| 2936211 | 3/1981 | Fed. Rep. of Germany | 568/9 |
| 3119490 | 5/1988 | Japan | 568/9 |
| 0121241 | 5/1989 | Japan | 562/477 |

OTHER PUBLICATIONS

CA 113(15):132186b, "Preparation of (diphenylpropyl)-triazole derivatives as Aromokian Inhibitors and Plant Antiluregal Agents", (Boyl I Au), EP 354689A1, Feb. 14, 1990. Abstract only.

Johnson, A. W. et al., Chemistry Department University of North Dakota, "Chemistry of Ylids. XII. Effect of Phosphorus Substituents on the Stereochemistry of the Wittig Reaction", vol. 31, Jan. 1966, pp. 334–336.

Primary Examiner—José G. Dees
Assistant Examiner—Keith MacMillan

[57] ABSTRACT

The invention provides fungicidal compositions containing benzyl-tris(aryl)-phosphonium salts of the general formula

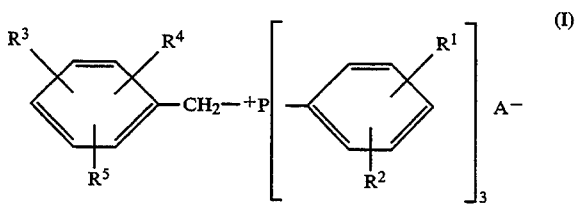

in which $R^1$ represents an optionally substituted alkyl or alkoxy group; $R^2$ represents a hydrogen atom or an optionally substituted alkyl group; $R^3$, $R^4$ and $R^5$ independently represent a hydrogen or halogen atom or an optionally substituted alkyl or alkoxy group; and $A^-$ represents an anion processes for the preparation of such compounds. Certain of the compounds of formula I are novel and the invention therefore also provides processes for the preparation of such compounds and their use as fungicides.

6 Claims, No Drawings

FUNGICIDAL COMPOSITIONS CONTAINING BENZYL-TRIS(ARYL)PHOSPHONIUM SALTS

The present invention relates to fungicidal compositions containing benzyl-tris(aryl)phosphonium compounds, some which are novel, and their use as fungicides.

It is known that many quaternary phosphonium salts are useful as bactericides (Jap. 18876/65), herbicides (U.S. Pat. No. 3,268,323; EP 73574) and nematicides (SA 67/3603). Also, U.S. Pat. No. 4,251,522 and EP 28493 disclose certain phenoxybenzylphosphonium salts and tris(aryl)alkyl phosphonium salts respectively which have fungicidal activity. However, many of these compounds, particularly alkyl-triphenyl phosphonium salts, show moderate to strong phytotoxicity when applied to plants or their activity against various fungi is too weak at non-phytotoxic concentrations. In particular, such phytopathogenic fungi as *Botrytis cinerea* or *Plasmopara viticola* are not well controlled by these compounds.

In addition, J. Org. Chem., 31(1), (1966), 334–336 discloses 4-methoxybenzyl-tris(4-methoxyphenyl)phosphonium bromide, U.S. Pat. No. 4,187,300 discloses 3,4-dichlorobenzyl-tris(3-methylphenyl)phosphonium chloride, benzyl-tris(2-methylphenyl)phosphonium chloride and 2,4-dichlorobenzyl-tris(4-methylphenyl)-phosphonium phosphnium iodide and Z. anorg. allg. Chem., 551, (1987), 179–190 discloses benzyl-tris(4-t-butylphenyl)phosphonium hydrogen diiodide. However, none of these documents gives any indication that the compounds disclosed therein possess any fungicidal activity.

It has now been found that substituted benzyl-tris-(aryl)phosphonium salts surprisingly exhibit excellent fungicidal activity, particularly against *Botrytis cinerea* and *Plasmopara viticola*, at low dosages and without phytotoxicity.

According to the present invention there is therefore provided a fungicidal composition which comprises a carrier and, as active ingredient, a compound of the general formula

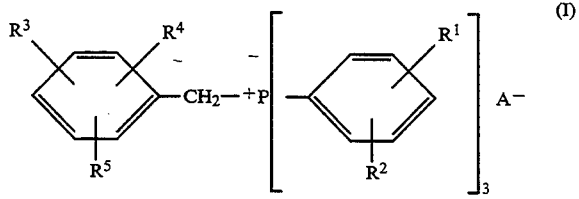

in which $R^1$ represents an optionally substituted alkyl or alkoxy group; $R^2$ represents a hydrogen atom or an optionally substituted alkyl group; $R^3$, $R^4$ and $R^5$ independently represent a hydrogen or halogen atom or an optionally substituted alkyl or alkoxy group; and $A^-$ represents an anion.

When the compounds of this invention contain an alkyl substituent group, this may be linear or branched and may contain up to 12, preferably up to 6, and especially up to 4, carbon atoms.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms.

It is preferred that $R^1$ represents a $C_{1-6}$ alkyl or $C_{1-6}$ alkoxy group. More preferably, $R^1$ represents a $C_{1-4}$ alkyl or $C_{1-4}$ alkoxy group.

Preferably, $R^2$ represents hydrogen atom or a $C_{1-6}$ alkyl, especially a $C_{1-4}$ alkyl, group.

It is preferred that $R^3$, $R^4$ and $R^5$ independently represent a hydrogen or halogen, that is, a fluorine, chlorine, bromine or iodine, atom or a $C_{1-4}$ alkyl or $C_{1-4}$ alkoxy group.

Preferably, $A^-$ is an anion of an inorganic or organic acid. However, anions are preferred which are not phytotoxic. Examples of such anions are halides, especially chloride and iodide, thiocyanates, salicylates, saccharinares and sulphonic acid anions, especially optionally substituted alkyl or aralkyl sulphonates. Of these, chloride, iodide, thiocyanate and sulphonic acid anions are especially preferred.

The compounds according to general formula I are oils, gums, or, predominantly, crystalline solid materials at room temperature. They are superior by their valuable fungicidal properties. For example, they can be used in agriculture or related fields for the control of phytopathogenic fungi such as *Botrytis cinerea* or *Plasmopara viticola* in vine. The compounds of general formula I according to the invention possess a high fungicidal activity within a wide concentration range and may be used especially in agriculture without any difficulties.

Good results in terms of the control of phytopathogenic fungi have been obtained with compounds of general formula I wherein $R^1$ represents a methyl, propyl, butyl, methoxy or butoxy group; $R^2$ represents a hydrogen atom or a methyl, particularly a 3-methyl, group; $R^3$, $R^4$ and $R^5$ independently represent a hydrogen, fluorine or chlorine atom or a methyl or methoxy group; and $A^-$ represents a chloride, iodide, thiocyanate, toluenesulphonate or dodecylsulphonate anion.

Certain compounds of formula I are novel per se and the present invention therefore also provides compounds of the general formula I as defined above with the provisos that (i) when $R^2$, $R^3$, $R^4$ and $R^5$ simultaneously represent a hydrogen atom, then $R^1$ does not represent a 2-methyl group when $A^-$ represents a chloride anion, and, $R^1$ does not represent a 4-tert-butyl group when $A^-$ represents a hydrogen diiodide anion;

(ii) when $R^2$, $R^4$ and $R^5$ simultaneously represent a hydrogen atom and $A^-$ represents a bromide anion, then $R^1$ and $R^3$ do not simultaneously represent a 4-methoxy group; and (iii) when $R^2$ and $R^5$ both represent a hydrogen atom and $R^4$ represents a 4-chloro group, then $R^1$ does not represent a 3-methyl group when $R^3$ represents a 3-chloro group and $A^-$ represents a chloride anion, and, $R^1$ does not represent a 4-methyl group when $R^3$ represents a 2-chloro group and $A^-$ represents an iodide anion.

The present invention also provides a process for the preparation of a compound of formula I as defined in the preceding paragraph which comprises reacting a compound of the general formula

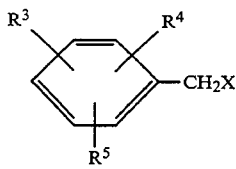

in which $R^3$, $R^4$ and $R^5$ are as hereinbefore defined and X represents a chlorine or bromine atom, with a compound of the general formula

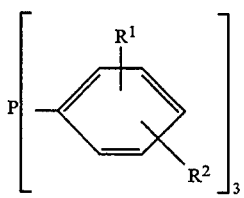

in which $R^1$ and $R^2$ are as hereinbefore defined to produce a compound of formula I in which $A^-$ is $X^-$, optionally followed by exchange of $X^-$ for another anion $A^-$.

The reaction of the benzyl halide II with the phosphine III can be carried out in a way known in principle, whereby, if practicable, inert solvents which do not interfere with the reaction or solvents which promote the reaction are used, e.g. acetonitrile, acetone, toluene, dioxane, tetrahydrofuran. Also mixtures of such solvents, e.g. toluene and acetonitrile, are advantageous. Depending on the reactivity of the components, the reaction may be carried out with cooling, at room temperature or at elevated temperature up to the boiling point of the reaction mixture. Generally, temperatures above 50° C. are preferred. The starting materials of formulae II and III are known compounds or may be prepared by processes analogous to known processes.

The solubility of a compound according to general formula I depends on the substituents $R^1$ to $R^5$ and the anion $A^-$. For example, compounds with $R^1=CH_3$ or $C_2H_5$ and $A^-=Cl^-$ or $Br^-$ are only slightly soluble in toluene, whereas the chlorides, iodides and thiocyanates with $R^1 \geq$ propyl show moderate to good solubility in this solvent.

The compounds according to the invention are excellent fungicides, especially for the control of phytopathogenic fungi in agriculture or related fields. They are particularly useful for the control of *Botrytis cinerea* or *Plasmopara viticola*. Due to the excellent plant tolerance, the compounds can be used in all cultivation of plants where infection by the controllable fungi is not desired, e.g. vine, strawberries, beans, ornamental plants.

The invention also provides a method of making a fungicidal composition which comprises bringing a compound of formula I as defined above into association with at least one carrier. Such a composition may contain a single compound or a mixture of several compounds of the present invention. Preferably, at least one carrier in a composition according to the invention is a surface-active agent. For example, the composition may contain at least two carriers, at least one of which is a surface-active agent.

The compounds according to general formula I may be used as such, however, they are preferably used as compositions comprising, besides the compounds according to the invention, adjuvants and auxiliaries which are known for formulation purposes and are manufactured into e.g. emulsion concentrates, solutions which may be sprayed directly or diluted, diluted emulsions, wettable powders, soluble powders, dusts, granulates or microencapsulates by well-established procedures. Because of the ionic nature of the compounds according to general formula I special attention has to be paid to the compatibility of the formulation adjuvants and auxilliaries with the active ingredients. In general, non-ionic substances are preferred. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulphoxide, alkyl formamides, epoxidised vegetable oils, e.g. epoxidised coconut or soybean oil, water.

Solid carriers, which may be used for dusts or dispersible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Suitable surface-active substances may be non-ionic, anionic or cationic tensides with good dispersing, emulgating and wetting properties depending on the nature of the compounds according to general formula I to be formulated. Due to the ionic nature of the active ingredients, non-ionic tensides are preferred over anionic or cationic synthetic tensides. Tensides may also mean mixtures of tensides.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

As anionic surface-active substances synthetic tensides are preferably used, especially fatty sulphonates, fatty sulphates, sulphonated benzimidazole derivatives or alkyl aryl sulphonates.

The fatty sulphates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Cationic tensides preferably are quarternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The tensides generally used for compositions are disclosed in such publications as:

"McCutheon's Detergents and Emulsifiers Annual", MC Publishing Corp., Ridgewood, NJ, USA 1981;

H. Stache, "Tensid-Taschenbuch", 2nd ed., C. Hanser, Munich, Vienna, 1981;

M. and J. Ash, "Encyclopedia of Surfactants", vol. I-III, Chemical Publishing Co., New York, NY, USA 1980-1981.

The pesticidal compositions usually comprise 0.1% to 95%, preferably 0.1% to 80% of at least one compound according to general formula I, 1% to 99.9% of a solid or liquid adjuvant and 0% to 25%, preferably 0.1% to 25%, of a tenside.

The compositions usually comprise:

| Emulsion Concentrates: | |
|---|---|
| Active ingredient: | 1% to 20%, preferably 5% to 10% |
| Surface-active substance: | 1% to 30%, preferably 1% to 20% |
| Liquid carrier: | 50% to 94%, preferably 70% to 85% |
| Suspension-Concentrates: | |
| Active ingredient: | 5% to 75%, preferably 10% to 50% |
| Water: | 94% to 24%, preferably 88% to 30% |
| Surface-active substance: | 1% to 40%, preferably 2% to 30% |
| Wettable Powder: | |
| Active ingredient: | 0.5% to 90%, preferably 1% to 80% |
| Surface-active substance: | 0.5% to 20%, preferably 1% to 15% |
| Solid carrier: | 5% to 95%, preferably 15% to 90% |
| Dusts: | |
| Active ingredient: | 0.1% to 10%, preferably 0.1% to 1% |
| Solid carrier: | 99.9% to 90%, preferably 99.9% to 99% |

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions may also comprise other auxiliaries such as stabilizers, defoamers, viscosity controlling agents, thickeners, adhesives, fertilisers or other active ingredients to obtain special effects.

The invention still further provides the use as a fungicide of a compound of the general formula I as defined above or a composition as defined above and a method of combating fungi at a locus which comprises treating the locus, which may be for example plants subject to or subjected to fungal attack, seeds of such plants or the medium in which such plants are growing or are to be grown, with such a compound or composition.

The following examples further illustrate the invention.

EXAMPLES

Example 1

Preparation of 2,4-dichlorobenzyl-tris-p-tolylphosphonium chloride: ($R^1$=4-$CH_3$; $R^2$=H; $R^3$=2-Cl; $R^4$=4-Cl; $R^5$=H; $A^-$=$Cl^-$)

Method A

A solution of 2,4-dichlorobenzyl chloride (2.93g, 0.015 mol) and tri-p-tolyl phosphine (4.55 g, 0.015 mol) in toluene (50 ml) was refluxed for 15 hours. After the reaction mixture was chilled to 20° C., the crystallised 2,4-dichlorobenzyl tris-p-tolyl-phosphonium chloride was collected by vacuum filtration, washed with acetonitirile and dried.

Yield: 5.5 g (73% of theoretical)

Mp.: 253°–255° C.

$C_{28}H_{26}Cl_3P$(499.86):

Calcd: C 67.28, H 5.24, Cl 21.28, $Cl^-$ 7.10, P 6.20%;

Found: C 67.11, H 5.30, Cl 21.00, $Cl^-$ 7.20, P 6.36%.

Method B

A solution of 2,4-dichlorobenzyl chloride (2.93 g, 0.015 mol) and tri-p-tolyl phosphine (4.55 g, 0.015 mol) in acetonitrile (100 ml) was refluxed for 5 hours. Then the solvent was removed by distillation, first under normal, later under reduced pressure. The residue crystallised upon trituration with diisopropyl ether. The product was collected by vacuum filtration, washed with diisopropylether and dried.

Yield: 7.2 g (96% of th.)

Mp: 253°–255° C.

The compounds of Table 1 were synthesised analogously to method A or B. In all cases, $R^2$=$R^5$=H.

TABLE 1

$R^3$-phenyl(R^4)-CH_2-+P-[phenyl(R^1)]_3 Cl^-

| No. | $R^1$ | $R^3$ | $R^4$ | mp. (°C.) |
|---|---|---|---|---|
| 1 | 3-CH$_3$ | 2-Cl | 4-Cl | 223–225 |
| 2 | 4-CH$_3$ | 2-Cl | 6-Cl | 297–300 |
| 3 | 3-CH$_3$ | 3-Cl | 4-Cl | 220–222 |
| 4 | 4-CH$_3$ | 3-Cl | 4-Cl | 265–266 |
| 5 | 4-CH$_3$ | 2-CH$_3$ | H | 280–282 |
| 6 | 4-CH$_3$ | 3-CH$_3$ | H | 249–251 |
| 7 | 4-CH$_3$ | 4-CH$_3$ | H | 263–265 |
| 8 | 4-CH$_3$ | 4-CH$_3$ | 3-Cl | 163–165 |
| 9 | 4-CH$_3$O | 2-Cl | 4-Cl | 88–90 |
| 10 | 4-CH$_3$O | 2-Cl | 6-Cl | 253–255 |
| 11 | 4-CH$_3$O | 2-F | 4-Cl | 88–90 |
| 12 | 4-CH$_3$ | 4-CH$_3$O | H | 213–215 |

EXAMPLE 2

Preparation of 2,4-dichlorobenzyl-tris(p-tertiary-butylphenyl)phosphonium chloride: ($R^1$=4-C(CH$_3$)$_3$; $R^2$=H; $R^3$=2-Cl; $R^4$=4-Cl; $R^5$=H; $A^{-1}$=Cl$^-$)

A solution of 2,4-dichlorobenzyl chloride (4.5 g, 0.023 mol) and tris(p-tertiary-butylphenyl)-phosphine (9.8 g, 0.023 mol) in a mixture of acetonitrile (50 ml) and toluene (50 ml) was refluxed for 5 hours. After evaporation of the solvent in vacuo, the oily residue was triturated with diisopropylether for 10 min whereby a crystal-pulp formed. After 1 hour, the crystalline 2,4-dichlorobenzyl-tris(p-tertiary-butylphenyl)-phosphonium chloride was collected by vacuum filtration, washed with diisopropyl ether and dried.

Yield: 14.3 g,(95% of th.)
Mp.: 258°–260° C.
C$_{37}$H$_{44}$Cl$_3$P(626.10):
Calcd: C 70.98, H 7.08, Cl 16.99, Cl$^-$ 5.66, P 4.95%;
Found: C 71.08, H 7.19, Cl 16.80, Cl$^-$ 5.62, P 4.80%

In analogy to this example, the compounds of table 2 were prepared. In all cases, $R^2$=$R^5$=H.

TABLE 2

| No. | $R^1$ | $R^3$ | $R^4$ | mp. (°C.) |
|---|---|---|---|---|
| 1 | 4-t-butyl | 2-Cl | 5-Cl | >200 |
| 2 | 4-t-butyl | 2-Cl | 6-Cl | 263–265 |
| 3 | 4-t-butyl | 3-Cl | 4-Cl | 273–275 |
| 4 | 4-t-butyl | 2-F | 4-Cl | 195–197 |
| 5 | 4-t-butyl | 4-CH$_3$ | H | 263–265 |
| 6 | 4-t-butyl | 4-CH$_3$ | 3-Cl | 268–270 |
| 7 | 4-t-butyl | H | H | 232–234 |
| 8 | 4-t-butyl | 4-Cl | H | 255–257 |
| 9 | 4-t-butyl | 2-Cl | H | 148–150 |
| 10 | 4-i-propyl | 2-Cl | 4-Cl | oil |
| 11 | 4-i-propyl | 2-Cl | 6-Cl | 70–75 |
| 12 | 4-i-propyl | 3-Cl | 4-Cl | oil |
| 13 | 4-n-butoxy | 2-Cl | 4-Cl | gum |

EXAMPLE 3

Preparation of 2,4-dichlorobenzyl-tris-p-tolylphosphonium iodide: ($R^1$=4-CH$_3$; $R^2$=H; $R^3$=2-Cl; $R^4$=4-Cl; $R^5$=H; $A^-$=I$^-$)

Potassium iodide (0.83 g, 5 mmol), dissolved in methanol (10 ml), was added to a solution of the 2,4-dichlorobenzyl-tris-p-tolyl-phosphonium chloride (2.5 g, 5 mmol) obtained in Example 1 in methanol (50 ml) and the mixture kept at 40°–50° C. for 1 hour whereby potassium chloride precipitated. After evaporation of the solvent in vacuo, the residue was triturated with acetone (30 ml). The insoluble material was filtered off and the filtrate evaporated to dryness. The glassy residue slowly crystallised.

Yield: 2.9 g (98% of th.)
Mp.: 212°–215° C.
C$_{28}$H$_{26}$Cl$_2$IP (591.31) Calcd: I 21.46%; Found: I 21.30%

The compounds of tables 3a, b, c and d were prepared in analogy to Example 3, however, in some cases ethyl acetate or p-dioxane had to be added in order to obtain a clear solution in the beginning. In all cases $R^2$-$R^5$=H.

TABLE 3a

| No. | $R^1$ | $R^3$ | $R^4$ | mp. (°C.) |
|---|---|---|---|---|
| 1 | 4-CH$_3$ | 2-Cl | 6-Cl | 240–242 |
| 2 | 4-CH$_3$ | 3-Cl | 4-Cl | 247–249 |
| 3 | 4-CH$_3$O | 2-Cl | 4-Cl | 65–67 |
| 4 | 4-CH$_3$ | 3-CH$_3$ | H | 225–227 |
| 5 | 4-CH$_3$ | 2-CH$_3$ | H | 224–226 |
| 6 | 4-CH$_3$ | 4-CH$_3$ | H | 225–227 |
| 7 | 4-CH$_3$ | 4-CH$_3$ | 3-Cl | 244–246 |
| 8 | 4-i-propyl | 2-Cl | 4-Cl | oil |
| 9 | 4-i-propyl | 2-Cl | 6-Cl | oil |
| 10 | 4-i-propyl | 3-Cl | 4-Cl | oil |
| 11 | 4-t-butyl | H | H | 240–242 |
| 12 | 4-t-butyl | 4-Cl | H | 299–302 |
| 13 | 4-t-butyl | 2-Cl | H | 230–233 |
| 14 | 4-t-butyl | 2-Cl | 4-Cl | 236–238 |
| 15 | 4-t-butyl | 2-Cl | 6-Cl | 238–240 |
| 16 | 4-t-butyl | 3-Cl | 4-Cl | 260–262 |
| 17 | 4-n-butoxy | 2-Cl | 4-Cl | 115–117 |
| 18 | 4-t-butyl | 4-CH$_3$ | H | 273–275 |
| 19 | 4-t-butyl | 4-CH$_3$ | 3-Cl | 253–255 |
| 20 | 4-CH$_3$ | 4-CH$_3$O | H | 204–206 |

TABLE 3b

| No. | $R^1$ | $R^3$ | $R^4$ | mp. (°C.) |
|---|---|---|---|---|
| 1 | 4-CH$_3$ | 2-Cl | 4-Cl | gum |
| 2 | 4-CH$_3$ | 2-Cl | 6-Cl | 228–230 |
| 3 | 4-CH$_3$ | 3-Cl | 4-Cl | 161–163 |
| 4 | 4-CH$_3$O | 2-Cl | 4-Cl | gum |
| 5 | 4-CH$_3$ | 3-CH$_3$ | H | 152–154 |

TABLE 3b-continued

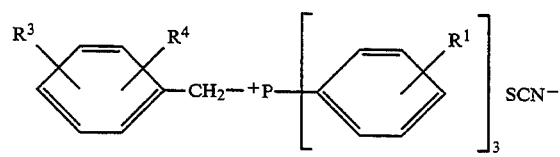

| No. | R¹ | R³ | R⁴ | mp. (°C.) |
|---|---|---|---|---|
| 6 | 4-CH₃ | 2-CH₃ | H | 135–137 |
| 7 | 4-CH₃ | 4-CH₃ | H | 195–197 |
| 8 | 4-CH₃ | 4-CH₃ | 3-Cl | 163–165 |
| 9 | 4-i-propyl | 2-Cl | 4-Cl | oil |
| 10 | 4-i-propyl | 2-Cl | 6-Cl | oil |
| 11 | 4-i-propyl | 3-Cl | 4-Cl | oil |
| 12 | 4-t-butyl | H | H | 214–216 |
| 13 | 4-t-butyl | 4-Cl | H | 226–228 |
| 14 | 4-t-butyl | 2-Cl | H | 128–130 |
| 15 | 4-t-butyl | 2-Cl | 4-Cl | 222–223 |
| 16 | 4-t-butyl | 2-Cl | 6-Cl | 231–232 |
| 17 | 4-t-butyl | 3-Cl | 4-Cl | 248–250 |
| 18 | 4-n-butoxy | 2-Cl | 4-Cl | gum |
| 19 | 4-t-butyl | 4-CH₃ | H | 219–221 |
| 20 | 4-t-butyl | 4-CH₃ | 3-Cl | 192–193 |
| 21 | 4-CH₃ | 4-CH₃O | H | 160–162 |

TABLE 3c

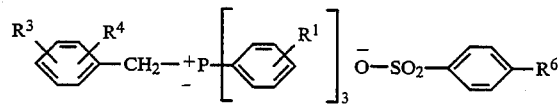

| No. | R¹ | R³ | R⁴ | R⁶* | mp. (°C.) |
|---|---|---|---|---|---|
| 1 | 4-CH₃ | 2-Cl | 4-Cl | —CH₃ | gum |
| 2 | 4-CH₃ | 2-Cl | 4-Cl | —C₁₂H₂₅ | 115–118 |
| 3 | 4-CH₃ | 2-Cl | 6-Cl | —C₁₂H₂₅ | wax |
| 4 | 4-CH₃ | 3-Cl | 4-Cl | —CH₃ | gum |
| 5 | 4-CH₃ | 3-Cl | 4-Cl | —C₁₂H₂₅ | 75–77 |
| 6 | 4-t-butyl | 2-Cl | 4-Cl | —C₁₂H₂₅ | 70–73 |
| 7 | 4-t-butyl | 2-Cl | 6-Cl | —CH₃ | 204–206 |
| 8 | 4-t-butyl | 2-Cl | 6-Cl | —C₁₂H₂₅ | 83–85 |
| 9 | 4-t-butyl | 3-Cl | 4-Cl | —CH₃ | 231–233 |
| 10 | 4-t-butyl | 3-Cl | 4-Cl | —C₁₂H₂₅ | gum |
| 11 | 4-CH₃O | 2-Cl | 4-Cl | —CH₃ | 65–67 |
| 12 | 4-CH₃O | 2-Cl | 4-Cl | —C₁₂H₂₅ | oil |
| 13 | 4-n-butoxy | 2-Cl | 4-Cl | —CH₃ | gum |

*Dodecylsulphonates also comprise other alkylsulphonates (C₁₀–C₁₄)

TABLE 3d

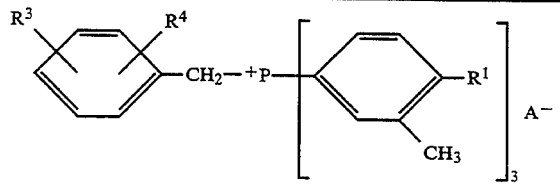

| No. | R¹ | R³ | R⁴ | A⁻ | mp. (°C.) |
|---|---|---|---|---|---|
| 1 | CH₃ | 2-Cl | 4-Cl | Cl | gum |
| 2 | CH₃ | 2-Cl | H | Cl | oil |
| 3 | OCH₃ | 2-Cl | 4-Cl | Cl | 226–228 |
| 4 | OCH₃ | 2-Cl | 4-Cl | SCN | 216–217 |
| 5 | CH₃ | 2-Cl | 6-Cl | Cl | 223–225 |
| 6 | CH₃ | 2-CH₃ | H | Cl | 224–226 |
| 7 | CH₃ | 4-CH₃ | H | Cl | 248–250 |
| 8 | CH₃ | 2-Cl | 6-Cl | SCN | 144–146 |
| 9 | CH₃ | 2-Cl | 6-Cl | I | 208–210 |

EXAMPLE 4

Emulsion concentrates:

The phosphonium salts according to formula I were formulated into emulsion concentrates by dissolving them in an appropriate solvent containing ethoxylated castor oil as surfactant. Subsequently, insoluble inorganic contaminations of the active ingredient were removed by filtration.

| Type A (a.i. insoluble in toluene): | |
|---|---|
| active ingredient: | 200 g/l |
| ethoxylated castor oil: | 100 g/l |
| tetrahydrofurfuryl alcohol: | 793 g/l |
| density: | 1.09 kg/l |
| Type B (a.i. soluble in toluene): | |
| active ingredient: | 10% (w/w) |
| ethoxylated castor oil: | 10% (w/w) |
| aromatic hydrocarbons: | 80% (w/w) |

EXAMPLE 5

A) Fungicidal activity against *Botrytis cinerea* on *Vicia faba* L.

Plants of *Vicia faba* L. var. Ackerperle were grown to the 2-2.5-leaf stage. Then they were treated with a solution of the test compound (100, 50, 25, 12.5 and 6.25 ppm) in water/acetone/Triton X. After 3–4 days, the plants were infected with a spore suspension of *Botrytis cinerea* (containing 2% of Biomalz) and then kept in a climatic chamber in the dark at a relative humidity of 100% for about 4 days. For the assessment the following scheme was used (Table 4):

0 = no infection
1 = 1–10% infection
2 = 11–40% infection
3 = 41–100% infection

TABLE 4

| Compound | Concentration a.i. [ppm] | | | |
|---|---|---|---|---|
|  | 50 | 25 | 12.5 | 6.25 |
| table 1, no. 7 | 1 | 1 | 1 | 1 |
| Example 2 | 2 | 2 | 3 | 3 |
| table 2, no. 2 | 1 | 2 | 3 | 3 |
| table 3a, no. 4 | 1 | 1 | 1 | 2 |
| table 3a, no. 5 | 1 | 1 | 1 | 1 |
| table 3a, no. 6 | 1 | 1 | 1 | 2 |
| table 3a, no. 15 | 1 | 1 | 2 | 2 |
| table 3b, no. 15 | 1 | 1 | 1 | 2 |
| table 3b, no. 16 | 1 | 1 | 2 | 3 |
| table 3d, no. 5 | 2 | 2 | 2 | 2 |
| table 3d, no. 6 | 2 | 2 | 2 | 2 |
| table 3d, no. 7 | 2 | 2 | 3 | 3 |
| table 3d, no. 8 | 1 | 1 | 1 | 2 |
| table 3d, no. 9 | 1 | 1 | 1 | 2 |

B) Fungicidal activity against *Venturia inaequalis* on *Malus* sp.

Apple cuttings of the variety Morgenduft, which are about 6 weeks old, were treated with a solution of the test compound (400 ppm) in water/acetone/Triton X. After 24 hours the plants were infected with a conidia suspension of *Venturia inaequalis* (c. 50,000 conidia/ml), incubated in a dark climatic chamber at a relatively humidity of 100% for 48 hours and, then, kept at a relative humidity of 95–99%, and temperatures of 18°–20° C. during the day and 13° C. during the night for about 14 days. For assessment the same scheme as for A) was used (Table 5).

TABLE 5

| Compound | Concentration [400 ppm] |
|---|---|
| table 1, no. 7 | 2.8 |
| Example 2 | 3.0 |
| table 2, no. 2 | 2.8 |
| table 3a, no. 4 | 2.8 |
| table 3a, no. 5 | 2.8 |
| table 3a, no. 6 | 2.0 |
| table 3b, no. 4 | 1.3 |
| table 3b, no. 15 | 1.3 |
| table 3b, no. 16 | 2.3 |

We claim:

1. A method for the control of fungus which comprises contacting said fungus with a fungicidally effective amount of a compound of the formula:

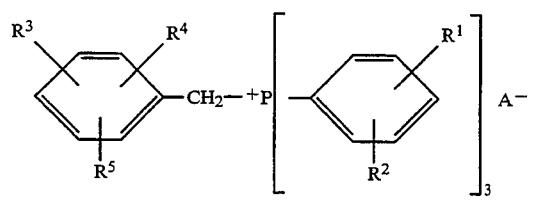

in which $R^1$ represents an optionally substituted $C_{1-12}$ alkyl or $C_{1-12}$ alkoxy group;

$R^2$ represents a hydrogen atom or an optionally substituted $C_{1-12}$ alkyl group;

$R^3$, $R^4$ and $R^5$ independently represent a hydrogen or halogen atom or an optionally substituted $C_{1-12}$ alkyl or $C_{1-12}$ alkoxy group; and $A^-$ represents a halide, thiocyanate, salicylate, saccharinate or toluenesulphonate or dodecylbenzenesulphonate anion; and said optional substituents being selected form the group consisting of halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, $C_{1-4}$ alkanoyl, $C_{1-4}$ alkylthio, $C_{1-4}$ alkylsulphinyl, $C_{1-4}$ alkylsulphonyl, carbamoyl and $C_{1-4}$ alkylamido groups.

2. A method according to claim 1 in which $R^1$ represents a $C_{1-6}$ alkyl or $C_{1-6}$ alkoxy group.

3. A method according to claim 1 in which $R^2$ represents a hydrogen atom or a $C_{1-6}$ alkyl group.

4. A method according to claim 1 in which $R^3$, $R^4$ and $R^5$ independently represent a hydrogen or halogen atom or a $C_{1-4}$ alkyl or $C_{1-4}$ alkoxy group.

5. A composition according to claim 1 in which $A^-$ represents a chloride or iodide anion.

6. A method according to claim 1, in which $R^1$ represents a methyl, propyl, butyl, methoxy or butoxy group; $R^2$ represents a hydrogen atom or a methyl group; $R^3$, $R^4$ and $R^5$ independently represent a hydrogen, fluorine or chlorine atom or a methyl or methoxy group and $A^-$ represents a chloride, iodide, thiocyanate toluenesulphonate or dodecylphenylsulphonate anion.

* * * * *